United States Patent [19]

Metz et al.

[11] 4,073,918

[45] Feb. 14, 1978

[54] PHENOXYALKYLCARBOXYLIC ACID AMIDES OF SUBSTITUTED THIAZOLIDINECARBOXYLIC ACIDS AND THEIR UTILIZATION IN MEDICAMENTS

[75] Inventors: Gunter Metz, Blaubeuren; Manfred Specker, Ehigen, Donau, both of Germany

[73] Assignee: Ludwig Merckle KG, Blaubeuren, Germany

[21] Appl. No.: 616,890

[22] Filed: Sept. 25, 1975

[30] Foreign Application Priority Data

Sept. 26, 1974 Germany ............................. 2446100

[51] Int. Cl.² .................. A61K 31/425; C07D 277/06
[52] U.S. Cl. ............................ 424/270; 260/306.7 C
[58] Field of Search .................. 260/306.7 C; 424/270

[56] References Cited

U.S. PATENT DOCUMENTS

| | | | |
|---|---|---|---|
| 3,498,996 | 3/1970 | Woodward | 260/306.7 C |
| 3,598,832 | 8/1971 | Woodward | 260/306.7 C |
| 3,880,872 | 4/1975 | Kukolja et al. | 260/306.7 C |
| 3,947,464 | 3/1976 | Asinger et al. | 260/306.7 C |
| 3,957,794 | 5/1976 | Baggiolini et al. | 260/306.7 C |

OTHER PUBLICATIONS

McOmie, "Protective Groups in Organic Chemistry", (1973), pp. 46–49.

*Primary Examiner*—R. Gallagher
*Assistant Examiner*—David E. Wheeler
*Attorney, Agent, or Firm*—Haseltine, Lake & Waters

[57] ABSTRACT

Phenoxyalkylcarboxylic acid amides and their preparation is described. These compounds are useful as antihypercholesteremic agents.

6 Claims, No Drawings

PHENOXYALKYLCARBOXYLIC ACID AMIDES OF SUBSTITUTED THIAZOLIDINECARBOXYLIC ACIDS AND THEIR UTILIZATION IN MEDICAMENTS

The subject of the invention relates to new phenoxyalkylcarboxylic acid amides of thiazolidinecarboxylic acids having the following general formula (I)

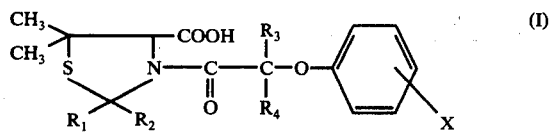

in which
X is a halogen atom or the trifluoromethyl group;
$R_1$ a hydrogen atom, a methyl group or (for $R_1 = R_2$) when taken together with the carbon atom to which they are attached form a spiro-cycloalkyl group with 4 to 6 carbon atoms;
$R_2$ a hydrogen atom, an aliphatic, straight-chained or branched alkyl group with 1 to 5 C-atoms; a phenyl-alkyl group; a straight-chained or branched, or with phenoxyalkylcarboxylic acid estered oxyalkyl group containing 1 through 5 C-atoms; an alkylcarboxylic acid or alkylcarboxylic acid alkylester group with 1 through 3 C-atoms, an aminomethyl group or with phenylalkylcarboxylic acid or phenoxyalkylcarboxylic acid N-methylamide group;
$R_3$ is a hydrogen atom; an aliphatic straight-chained alkyl group containing 1 through 5 C-atoms, or a halophenoxy group;
$R_4$ is a hydrogen atom or an aliphatic, straight-chained or branched alkyl group with 1 through 5 C-atoms;

as well as usual pharmaceutical salts of the combination of the general formula (I).

The halogen atoms in question are fluoro and chloroatoms, preferably in o- and p-position, and the trifluoromethyl group, being preferably in m-position.

Examples of suitable alkyl groups are methyl, ethyl, propyl, isopropyl, n-butyl, sec-butyl, tert-butyl, or the n-pentyl group, and branched pentyl groups. Preferred are alkyl groups with 1 to 3 C-atoms. The methyl group is particularly preferred.

Preferred halogen substituted phenoxylalkylcarboxylic acid esters possess 1 to 7, preferably 1 to 5, C-atoms in the alkylcarboxylic acid group. Of the alkylcarboxylic acids which contain more than 2 C-atoms, the branched alkyl groups are preferred.

For the salt formation, suitable pharmaceutically acceptable amines, as well as amino alcohols and amino esters, for example, dimethyl and diethyl amino ethanol or procaine base, as well as metals of the first, second and third major group of the periodic system, preferably Na, K, Ca, Mg and Al.

The invention further relates to a process for the production of phenoxyalkylcarboxylic acid derivatives having the general formula (I) which is characterized in that a phenoxyalkylcarboxylic acid having the general formula (II)

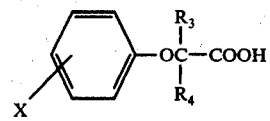

wherein
X, $R_3$ and $R_4$ are as previously defined, or a reactive derivative of said acid, in particular the acyl halides thereof, is reacted with a thiazolidinecarboxylic acid having the general formula (III)

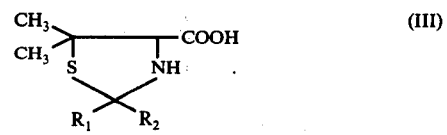

Where $R_2$ in the general formula (III) is an aminomethyl group substituted with phenoxyalkylcarboxylic acid, then this group is priorly introduced into the thiazolidine ring by means of a suitable phenoxyalkylcarboxylic acid amide acetal, and in the following reaction stage, as previously indicated, reacted with phenoxyalkylcarboxylic acid having the general formula (II).

The thiazolidinecarboxylic acids required as the starting compound having the general formula (III), are, in part, known compounds which are accessible through preparative methods known in the literature via the reaction of D-, L-, as well as D, L-penicillamine with ketones, aldehydes and acetals. (see "The Chemistry of Pencillin," Princeton University Press, 1949, Chapters 15 and 16). Compounds wherein $R_2$ is a phenoxyalkylcarboxylic acid N-methylamide group, are however to be considered as new.

The production of the thiazolidinecarboxylic acid having the general formula (III) is explained in more detail with respect to the following examples.

EXAMPLE 1

14.9 g (0.1 mole) D-penicillamine was suspended in 50 ml ethanol and brought to a pH value of 1 to 2 by means of isopropanol-HCl. Subsequently, 9.8 g (0.1 mole) cyclohexanone was added and the mixture heated for 1 hour under reflux.

After the distillation of the solvent medium by means of a rotational evaporator, the residue was crystallized using a little ethanol. 20.7 g was obtained (78% of theory) of 2-spirocyclohexyl-5, 5-dimethyl-thiazolidine-4-carboxylic acid hydrochloride of M.P. 212° C.

Titration with 0.1N HClO₄ showed a yield of 98.8% of theoretical.

EXAMPLE 2

29.8 g (0.2 mole) of D-penicillamine base was suspended in 200 ml ethanol and brought to pH 2 with isopropanol HCl. After the addition of 57.4 g (0.2 moles) 2-(p-chlorophenoxy)-propionyl-amido acetaldehyde dimethylacetal (M.P. 72°–73° C.) was heated for 1 hour under return flow, vaporized and the remainder crystallized from ethylacetate.

Obtained were 58.4 g (71.6% of theory) 2-[2-(p-chlorophenoxy)-propionamidomethyl]-5,5-dimethyl-thiazolidine-4-carboxylic acid hydrochloride, M.P. 186° C. Potentiometric titration with 0.1N HClO₄ showed a yield of 99.3% of theoretical.

EXAMPLES 3-17

In accordance with the procedure of Examples 1 and 2, through the use of appropriate starting materials, the following thiazolidinecarboxylic acids were produced:

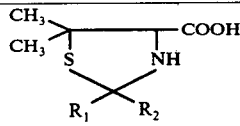

| Ex. | $R_1$ | $R_2$ | M.P. °C (as Hydrochloride) | Yield % |
|---|---|---|---|---|
| 3 | $CH_3$ | $CH_3$ | 195 | 81.2 |
| 4 | $CH_3$ | $CH_2C_6H_5$ | 192-193 | 87.4 |
| 5 | $CH_3$ | $CH_2CH_2CH_3$ | 171-72 | 91.2 |
| 6 | $CH_3$ | $C_2H_5$ | 192-93 | 77.6 |
| 7 | $CH_3$ | $CH_2CH_2COOH$ | 158-59 | 73.5 |
| 8 | $CH_3$ | $CH_2COOC_2H_5$ | 170-71 (154-55 Base) | 78.0 |
| 9 | Spirocyclohexyl | — | 212 | 87.4 |
| 10 | Spirocyclopentyl | — | 158-59 | 91.1 |
| 11 | H | H | 195-96 | 93.5 |
| 12 | H | $CH(CH_3)_2$ | 200-01 (134-35 Base) | 96.5 |
| 13 | H | $CH_2C_6H_5$ | 217-18 | 83.4 |
| 14 | H | $C(CH_3)_2-CH_2OH$ | 195-96 | 66.7 |
| 15 | H | $CH_2NH_2$ | 195-96 (2HCl) | 75.3 |
| 16 | H | $CH_2NHCOCH_2C_6H_5$ | 209-10 | 88.5 |
| 17 | H | $CH_2NHCOC(CH_3)_2-O-C_6H_4\text{-}pCl$ | 200-201 | 76.4 |

The amidization of the thiazolidinecarboxylic acids with phenoxyalkylcarboxylic acids mentioned in Examples 1 to 17 and having the general formula (II), was carried out pursuant to known preparative methods. For example, acid derivatives suitable for this amidation are, acidic chlorides and acid anhydrides.

The conversion with the thiazolidinecarboxylic acids was carried out hereby suitably in an anhydrous, inert solvent such as aromatic hydrocarbons or halohydrocarbon materials, optionally in the presence of suitable amines as acid receptors, such as, pyridine, quinoline, and tertiary amines. The reaction can be carried out at room temperature, as well as by heating. Preferably, the reaction is carried out at the reflux temperature of the solvent medium.

The amidization of the thiazolidinecarboxylic acids with phenoxyalkylcarboxylic acids, or suitable derivatives thereof, for example, the esters can also carried out under the addition of suitable catalysts, such as carbonyldiimidazole; dicyclohexylcarbodiimide, or a similar imide, under gentle conditions with good yields.

The mole relationship between the phenoxyalkylcarboxylic acid and the thiazolidine compound in the reaction mixture is preferably 1:1 to 2:1. The time for completion of the reaction ranged between 2 to 10 hours. The resulting amide having the general formula (I) can, after removal of the solvent so that remaining basic components, be produced in a pure form through suitable crystallization. Insofar as oily products are obtained, the content determination provided through potentiometric titration with 0.1 N NaOH in the raw product showed values over 97% of theory, so that no further purification need be further undertaken.

The production of the inventive compounds having the general formula (I) is described in the following Examples.

EXAMPLE 18

45.2 g (0.2 moles) 2,2,5,5-tetramethylthiazolidine-4-carboxylic acid hydrochloride (Example 3) was suspended in 300 ml chloroform with the addition of 40.4 g (0.4 mole) triethylamine and reacted in portions with 69.3 g (0.2 mole) 2-(p-chlorophenoxy)-propionic acid anhydride. After addition was completed, the mixture was heated for 5 hours under reflux. The mixture was then extracted with water saturated with gaseous hydrochloric acid, and the solvent media removed in the rotational evaporator. The remainder was crystallized out of a little ethanol. Obtained were 46.5 g. (63% of theory) 2,2,5,5-tetramethyl-3-[2-(p-chlorophenoxy)propionyl]-thiazolidine-4-carboxylic acid, M.P. 186°-187° C.

| Elementary analysis: | C | H | N | S | Cl |
|---|---|---|---|---|---|
| $C_{17}H_{22}ClNO_4S$ Theor.: | 54.92 | 5.97 | 3.77 | 8.62 | 9.53 |
| (M.W. 371.8) Found: | 54.69 | 6.09 | 3.62 | 8.39 | 9.55 |

EXAMPLE 19

45.2 g (0.2 mole) 2,2,5,5-tetramethyl-thiazolidine-4-carboxylic acid hydrochloride (Example 3) was suspended with 40.4 g triethylamine in 300 ml chloroform, and under stirring reacted with 50.0 g (0.2 mole) 2-(p-chlorophenoxy)-2-methylpropionyl acid chloride. The mixture was heated for 5 hours under reflux. The resulting clear solution was then washed with dilute hydrochloric acid and then with water. After the evaporation of the solvent media, the remaining residue was crystallized from aqueous alcohol. Obtained was 58.6 g (76% of theory) 2,2,5,5-tetramethyl-3-(2(p-chlorophenoxy)-2-methylpropionyl]-thiazolidine-4-carboxylic acid, M.P. 173°-74° C.

| Elementary Analysis: | C | H | N | S | Cl |
|---|---|---|---|---|---|
| $C_{18}H_{24}ClNO_4S$ Theor.: | 56.02 | 6.27 | 3.63 | 8.31 | 9.19 |
| (M.W. 385.9) Found: | 56.20 | 6.28 | 3.66 | 8.26 | 8.96 |

EXAMPLE 20

36.0 g (0.16 mole) of thiazolidinecarboxylic acid, according to Example 3, was suspended, along with 24.0 g (0.3 mole) of pyridine, in 200 ml chloroform and reacted with 31.0 g (0.15 mole) of p-chlorophenoxyacetyl chloride. After 4 hours heating of the mixture at 50° C, it was washed with dilute hydrochloric acid, and then with water. After evaporating the solvent media, the remainder was dissolved in a little chloroform and, through the addition of diisopropyl ether, brought to crystallization. This material was recrystallized out of aqueous methanol. Yield 36.0 g (65% of theory) 2,2,5,5-tetramethyl-3-(p-chlorophenoxyacetyl)-thiazolidine-4-carboxylic acid of M.P. 146°-47° C.

| Elementary Analysis: | C | H | N | S | Cl |
|---|---|---|---|---|---|
| $C_{16}H_{20}ClNO_4S$ | Theor.: 53.7 | 5.61 | 3.91 | 8.95 | 9.92 |
| (M.W. 357.8) | Found: 53.67 | 5.65 | 4.29 | 9.19 | 10.38 |

The potentiometric titration using 0.1N NaOH provided a content of 100.5% of theory.

| 3-Amino-3-methylbutanol salt: | M.P. 128-30° C |
|---|---|
| Diethylamino ethanol salt: | M.P. 121-22° C. |

EXAMPLE 21

17.0 g (0.04 mole) thiazolidinecarboxylic acid, according to Example 17, was dissolved, along with 6.3 g (0.08 mole) pyridine, in 50 ml chloroform and reacted with 8.2 g (0.04 mole) p-chlorophenoxyacetyl chloride and processed as previously described (Example 19).

A yield of 10.5 g (70% of theory) 2-[2-(p-chlorophenoxy)-2-methyl-propionylamidomethyl]-5,5-dimethyl-3-(p-chlorophenoxyacetyl)-thilazolidine-4-carboxylic acid was obtained, M.P. 158°-59° C.

| Elementary Analysis: | C | H | N | S | Cl |
|---|---|---|---|---|---|
| $C_{25}H_{28}Cl_2N_2O_6S$ | Theor.: 54.05 | 5.09 | 5.05 | 5.78 | 12.76 |
| (M.W. 555.5) | Found: 54.13 | 5.13 | 5.21 | 5.89 | 12.70 |

EXAMPLES 22-36

According to the process of Example 18, and using the corresponding starting compounds, the following amides of the thiazolidinecarboxylic acids having the general formula (I) were produced.

2-(p-chlorophenoxy)-2-methylpropionic acid ethyl ester (chlofibrate).

The acute oral toxicity of the inventive compounds of Examples 18 and 23 was tested on, respectively, five male and female laboratory rats each having a weight of 200 ± 20g. The compounds tested were prepared as suspension in 0.5 %-aqueous Tween 80-solution. The observation time period was 14 days. The determination of the $LD_{50}$-values was carried out pursuant to the methods of Litchfield and Wilcoxon.

| Compound | $LD_{50}$(mg/kg) | Effective limits (mg/kg) |
|---|---|---|
| Example 18 | > 5000 | |
| Example 23 | 4350 | 3680 - 5130 |
| Clofibrate | ca 1200 | (Literature reference) |

As is known from German Pat. No. 2,116,629, thiazolidinecarboxylic acid derivatives indicate a liver protective effect preferentially, having ascribing thereto the property of releasing organism SH-groups in the organism and to thereby effecting a stimulation of the nucleic acids and protein synthesis.

These properties are also shown by D-penicillamine, which could be indicated on the galactosamine-hepatitis-model of the rate (Arzneimittel-Forschung 23, 56, 1973).

As indicated from the last mentioned examination, the D-penicillamine shows also a satisfactory influence on lipid material exchange.

The beneficial effect of lipid material exchange is opposed by the known side effects of D-penicillamine such as allergic reactions, leukopenia or gastrointestinal disturbances, so that the therapeutical uses in the treatment of lipid material exchange disturbances with D-penicillamine, is minimized.

In contrast therewith, the inventive compounds having the general formula (I) show based on the normal lipemic as well as the hypercholesteremic rat models, a

| Ex. | X | $R_1$ | $R_2$ | $R_3$ | $R_4$ | M.P. ° C |
|---|---|---|---|---|---|---|
| 22 | p-Cl | $CH_3$ | $CH_2C_6H_5$ | H | $CH_3$ | 158 |
| 23 | p-Cl | | Spirocyclohexyl | H | H | 176 |
| 24 | p-Cl | | Spirocyclopentyl | H | H | 150[1] |
| 25 | p-Cl | | Spirocyclopentyl | H | $CH_3$ | 175-76 |
| 26 | o-Cl | | Spirocyclopentyl | H | H | 182-83 |
| 27 | p-Cl | | Spirocyclopentyl | $CH_3$ | $CH_3$ | 176-77[2] |
| 28 | p-F | | Spirocyclopentyl | H | H | 143-44 |
| 29 | p-Cl | $CH_3$ | $CH_2COOC_2H_5$ | H | H | 146-147 |
| 30 | p-Cl | $CH_3$ | $CH_2CH_2COOH$ | $CH_3$ | $CH_3$ | 175-76 |
| 31 | p-Cl | $CH_3$ | $CH_3$ | $OC_6H_4$-pCl | H | 153-54 |
| 32 | p-Cl | H | H | H | $CH_3$ | oily[3] |
| 33 | m-$CF_3$ | $CH_3$ | $CH_3$ | H | $CH_3$ | oily[4] |
| 34 | p-Cl | H | $CH_2NHCOCH_2OC_6H_4$-pCl | H | H | 203 |
| 35 | p-Cl | H | $CH_2NHCOCHOC_6H_4$-pCl<br>\|<br>$CH_3$ | H | $CH_3$ | 186-87 |
| 36 | p-Cl | H | $C(CH_3)_2CH_2$—OCO<br>\|<br>p-ClC$_6$H$_4$OCHCH$_3$ | H | $CH_3$ | oily[5] |

[1] Procaine salt M.P., 126-27° C
[2] Dimethylaminoethanol salt, M.P. 123-24° C
[3] 98.8% Yield (Titration with 0.1NNaOH); DC with minor spots
[4] 99.2% Yield (Titration with 0.1NNaOH); DC non-uniform
[5] 97.5% Yield (Titration with 0.1NNaOH); DC with minor spots The inventive compounds having the general formula (I), distinguish themselves by having extremely low toxicity. This is shown by comparison with the known distinct anti-lipemic and, in particular anti-cholesteremic effect. The effect, as shown by comparison, is opposite to the known anti-lipemic agent clofibrate, since clofibrate on the hypercholesteremic models through its exclusively endogenic effect, shows no more activity. This activity loss of clofibrate on the hyperlipemic demands is also found a number of times in the literature. The antilipemic activity of the inventive compounds, as well as that of clofibrate as the reference substance, was determined on a normal lipemic CFY-rat during an examination time period of 14 days. During this time, the animals received a normal laboratory diet. (Spratt's No. 1).

After a 4-day acclimatization period the animals orally received the test compound as a suspension in 1% tragacanth-solution, or the vehicle alone (control group). The control-group consisted of 20 animals, while the test groups contained 10 animals. 24 hours after the last administration, blood samples were taken for determining the serum triglycerides and serum cholesterol level. The results of this examination are complied in Table 1 below.

The hypercholesteremic test was carried out on the same animals and under the same examining conditions, as was carried out in the normal lipemic test. The animals received a normal laboratory diet (Spratt's No. 2), having added thereto 2% cholesterol and 1% cholic acid. The results of this test series are complied in Table 2 below.

As a pharmacological screening of the compounds pursuant to Examples 17, 18 and 21 indicated for 51 pharmacological parameters, no special side effects were seen and, in particular, the previously mentioned side effects of D-penicillamine were lacking. Merely in compounds according to Example 18 as determined on the mouse (100 mg/kg intraperitoneal) a small reduction of the abdominal tone was observed.

Table 1

| Group | Dose mg/kg | Normolipemic Test | | | |
|---|---|---|---|---|---|
| | | Serum Cholesterol | | Serum Triglycerides | |
| | | mg % | Lowering % | mg % | Lowering % |
| Control | — | 86.2 | — | 94.4 | — |
| Example 18 | 100 | 95.8 | — | 68.7* | 27.2 |
| | 300 | 95.3 | — | 82.5 | 12.6 |
| Example 19 | 100 | 93.1 | — | 75.2* | 20.3 |
| | 300 | 82.0 | 4.9 | 72.7* | 23.0 |
| Example 20 | 100 | 87.8 | — | 67.6** | 28.4 |
| | 300 | 73.0* | 15.3 | 66.0** | 30.1 |
| Control | — | 93.8 | — | 87.0 | — |
| Example 17 | 100 | 81.8 | 12.8 | 77.3 | 11.2 |
| | 300 | 81.5 | 13.1 | 91.2 | — |
| Control | — | 96.4 | — | 66.7 | — |
| Example 21 | 100 | 89.4 | 7.3 | 59.1 | 11.4 |
| | 300 | 90.8 | 5.9 | 72.4 | — |
| Control | — | 76.9 | — | 123.8 | — |
| Clofibrate | 300 | 56.1*** | 27.0 | 66.5*** | 46.3 |

Significance
*p < 0.005
** p < 0.01
*** p < 0.001

Table 2

| Group | Dose mg/kg | Hypercholesteremic Test | | | |
|---|---|---|---|---|---|
| | | Serum Cholesterol | | Serum Triglycerides | |
| | | mg % | Lowering % | mg % | Lowering % |
| Control | — | 591.6 | — | 64.4 | — |
| Example 18 | 100 | 412.9** | 30.2 | 71.4 | — |
| | 300 | 470.3** | 20.5 | 72.4 | — |
| Example 19 | 100 | 549.1 | 7.1 | 65.9 | — |
| | 300 | 595.6 | — | 66.0 | — |
| Example 20 | 100 | 503.9 | 14.8 | 88.1 | — |
| | 300 | 479.6* | 18.9 | 92.2 | — |
| Control | — | 318.9 | — | 86.0 | — |
| Example 17 | 100 | 353.8 | — | 85.0 | 1.2 |
| | 300 | 296.1 | 7.2 | 96.4 | — |
| Control | — | 453.3 | — | 54.2 | — |
| Example 21 | 100 | 501.2 | — | 51.0 | 5.9 |
| | 300 | 465.1 | — | 41.3* | 23.9 |
| Control | — | 358.6 | — | 86.4 | — |
| Clofibrate | 300 | 347.9 | 3.0 | 75.6 | 12.5 |

Significance
*p < 0.05
**p < 0.01

As the examination results indicated, the tested inventive compounds are, with respect to their endogeneous effects (Table 1), much less effective in comparison with clofibrate.

However, they exceed the clofibrate considerably with respect to the exogeneous effect (Table 2), which can be ascertained from the significant reduction in the increased cholesterol content. Due to these results, the inventive compounds of the general formula (I) are valuable therapeutics for the treatment of lipid material exchange disturbances as well as, in particular, illnesses in connection with increased cholesterol levels, for example, atherosclerosis.

The inventive medicaments containing one or more thiazolidinecarboxylic acid derivatives have a general formula (I), respectively their salts, as active media.

The utilization is carried out orally, preferably in the form of capsules or tablets which, as required, may contain usual pharmaceutical carrier means and aids.

The rectal application is preferably carried out in the form of the free acids or, respectively, their salts. For parenteral application the pharmaceutically employable salts are suitable, due to their improved solubilities.

The inventive compounds are administered in amounts of 300–1500 mg/day, preferably 450–900 mg/day.

A suitable preparation for oral administration of compounds of the present invention is in the form of capsules which contain, for example, 150 mg. of the product of Example 18, 30 mg. maize starch and 60 mg. lactose. These ingredients are blended and then filled into capsules.

We claim:

1. A compound selected from the group consisting of phenoxyalkylcarboxylic acid amides of thiazolidinecarboxylic acid having the formula (I)

$$\begin{array}{c}CH_3\\CH_3\end{array}\!\!\!\diagup\!\!\!\begin{array}{c}\phantom{x}\\S\end{array}\!\!\!\diagdown\!\!\!\begin{array}{c}\phantom{x}\\N\end{array}\!\!\!-\!\!\!\begin{array}{c}COOH\\|\\C\\|\\R_1\phantom{xx}R_2\end{array}\!\!\!-\!\!\!\begin{array}{c}\phantom{x}\\C\\\|\\O\end{array}\!\!\!-\!\!\!\begin{array}{c}R_3\\|\\C\\|\\R_4\end{array}\!\!\!-\!\!\!O\!\!\!-\!\!\!\bigcirc\!\!\!-\!\!\!Cl$$

wherein
$R_1$ is selected from the group consisting of a hydrogen atom and a methyl group,
$R_3$ and $R_4$ are selected from the group consisting of a hydrogen atom and a methyl group,
$R_2$ is selected from the group consisting of a hydrogen atom, a methyl group and a group having the formula (II)

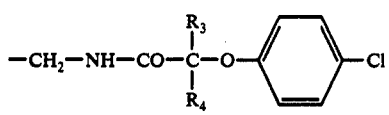

wherein $R_3$ and $R_4$ are as defined above, and the pharmaceutically acceptable salts thereof.

2. 2,2,5,5-Tetramethyl-3-[2-(p-chlorophenoxy)-propionyl]-thiazolidine-4-carboxylic acid.

3. 2,2,5,5-Tetramethyl-3-[2-(p-chlorophenoxy)-2-methylpropionyl]-thiazolidine-4-carboxylic acid.

4. 2,2,5,5-Tetramethyl-3-(p-chlorophenoxyacetyl)-thiazolidine-4-carboxylic acid.

5. A pharmaceutical hypocholoesteremic composition comprising, as active ingredient, a hypocholesteremic compound selected from the group consisting of phenoxyalkylcarboxylic acid amides of thiazolidinecarboxylic acid having the formula (I)

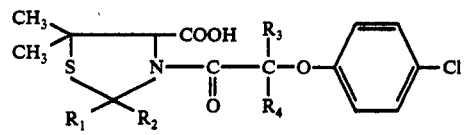

wherein
$R_1$ is selected from the group consisting of a hydrogen atom and a methyl group,
$R_3$ and $R_4$ are selected from the group consisting of a hydrogen atom and a methyl group,
$R_2$ is selected from the group consisting of a hydrogen atom, a methyl group and a group having the formula (II)

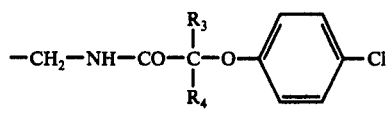

wherein $R_3$ and $R_4$ are as defined above, and the pharmaceutically acceptable salts thereof, in unit dosage forms for administering from 300–1500 mg/day, and a pharmaceutically acceptable carrier.

6. A pharmaceutical composition according to claim 5 which comprises, as active ingredient, 150 mg. of 2,2,5,5-Tetramethyl-3-[2-(p-chlorophenoxy)-propionyl]-thiazolidine-4-carboxylic acid, 30 mg. maize starch and 60 mg. lactose in capsule form.

* * * * *